(12) United States Patent
Xu et al.

(10) Patent No.: US 9,918,696 B2
(45) Date of Patent: Mar. 20, 2018

(54) METHOD AND APPARATUS FOR DETECTING A GAS POCKET USING ULTRASOUND

(71) Applicant: KONINKLIJKE PHILIPS N.V., Eindhoven (NL)

(72) Inventors: Jingping Xu, Shanghai (CN); Balasundar Iyyavu Raju, North Andover, MA (US); Sheng-Wen Huang, Ossining, NY (US); Shougang Wang, Ossining, NY (US); Emil George Radulescu, Ossining, NY (US); Shiwei Zhou, Yorktown Heights, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/900,191

(22) PCT Filed: Jan. 13, 2015

(86) PCT No.: PCT/EP2015/050438
§ 371 (c)(1),
(2) Date: Dec. 21, 2015

(87) PCT Pub. No.: WO2015/113806
PCT Pub. Date: Aug. 6, 2015

(65) Prior Publication Data
US 2016/0345931 A1   Dec. 1, 2016

(30) Foreign Application Priority Data

Jan. 30, 2014 (WO) ................ PCT/CN2014/071839
Apr. 15, 2014 (WO) ................ PCT/CN2014/075396
May 28, 2014 (EP) ..................................... 14170204

(51) Int. Cl.
*A61B 8/08* (2006.01)
*A61B 8/00* (2006.01)
(Continued)

(52) U.S. Cl.
CPC .............. *A61B 8/0833* (2013.01); *A61B 8/00* (2013.01); *A61B 8/14* (2013.01); *A61B 8/46* (2013.01);
(Continued)

(58) Field of Classification Search
CPC ..... A61B 8/0833; A61B 8/5223; A61B 8/461; A61B 8/469; A61B 8/5207; A61B 8/14; G01S 7/52038
See application file for complete search history.

(56) References Cited

U.S. PATENT DOCUMENTS 4,463,592 A * 8/1984 Flax ...................... G01N 29/30
  73/1.82
4,475,395 A * 10/1984 Flax ......................... G01H 3/00
  73/599

(Continued)

FOREIGN PATENT DOCUMENTS

EP   0150997 A2   8/1985
EP   2169426 A1   3/2010
(Continued)

OTHER PUBLICATIONS

Asrani: "Sonographic Diagnosis of Pneumoperitoneum Using the 'Enhancement of the Peritoneal Strip Sign.' A Prospective Study"; Emerg Radiol (2007), 14:29-39.
(Continued)

*Primary Examiner* — Peter Luong

(57) ABSTRACT

Existing gas pocket detection approaches are based on visual observations of B-mode ultrasound images showing comparisons between normal soft tissue and gas pockets, which
(Continued)

are time-consuming and dependent on operator experience. The present invention proposes an ultrasound system and a method of detecting a gas pocket. The ultrasound system comprises: an ultrasound probe (110) for transmitting an ultrasound signal toward the ROI and acquiring an ultrasound echo signal reflected from the ROI along a plurality of scanning lines; an obtaining unit (130) for obtaining a second harmonic component of the ultrasound echo signal for each depth of a plurality of depths along each scanning line of the plurality of scanning lines; and a deriving unit (140) for deriving a change in a center frequency of the second harmonic component along with the depth.

12 Claims, 7 Drawing Sheets

(51) Int. Cl.
G01S 7/52 (2006.01)
A61B 8/14 (2006.01)
(52) U.S. Cl.
CPC .............. A61B 8/461 (2013.01); A61B 8/467 (2013.01); A61B 8/469 (2013.01); A61B 8/48 (2013.01); A61B 8/52 (2013.01); A61B 8/5207 (2013.01); A61B 8/5215 (2013.01); A61B 8/5223 (2013.01); G01S 7/52038 (2013.01)

(56) References Cited

U.S. PATENT DOCUMENTS

| | | | | |
|---|---|---|---|---|
| 4,936,308 A * | 6/1990 | Fukukita | ............. | A61B 5/416 600/438 |
| 5,301,674 A * | 4/1994 | Erikson | ............. | A61B 8/488 600/447 |
| 6,095,980 A * | 8/2000 | Burns | ............. | A61B 8/481 600/453 |
| 6,174,286 B1 * | 1/2001 | Ramamurthy | ...... | G01S 7/52047 600/447 |
| 6,283,919 B1 | 9/2001 | Roundhill et al. | | |
| 6,458,083 B1 | 10/2002 | Jago et al. | | |
| 6,595,928 B2 | 7/2003 | Mansy et al. | | |
| 6,629,449 B1 | 10/2003 | Kline-Schoder et al. | | |
| 7,397,427 B1 * | 7/2008 | Rhoads | ............. | G01S 3/043 342/442 |
| 2003/0055337 A1 * | 3/2003 | Lin | ............. | G01S 15/8915 600/459 |
| 2010/0021026 A1 | 1/2010 | Collins et al. | | |

FOREIGN PATENT DOCUMENTS

| | | |
|---|---|---|
| JP | 2000312678 | 11/2000 |
| JP | 2007301286 A | 11/2007 |
| JP | 2011000383 A | 1/2011 |
| KR | 20120086598 | 8/2012 |
| WO | 2012139092 A2 | 10/2012 |
| WO | 2013025613 A1 | 2/2013 |

OTHER PUBLICATIONS

Bevan et al: "B-Scan Ultrasound Imaging of Thermal Coagulation in Bovine Liver: Frequency Shift Attenuation Mapping"; Ultrasound in Med & Biol., vol. 27, No. 6, pp. 809-817.
Bomann et al: "Abdominal A-Lines: A Simpler Sonographic Sign of Pneumoperitoneum?" Critical Ultrasound Journal, (2011), 3:pp. 41-42.
Chen et al : "Ultrasonography Is Superior T Plain Radiology in the Diagnosis of Pneumoperitoneum"; British Journal of Surgery 2002, 89, pp. 351-354.
Choi et al : "Sonographic Detection of Small Amounts of Free Peritoneal Gas in Beagle Dogs"; Journal of Vet. Med.Sci, 74(4), pp. 491-494, 2012.
Epelman et al: "Necrotizing Enterocolitis: Review of State-of-the-Art Imaging Findings With Pathologic Correlation"; Radiographics 2007, vol. 27, pp. 285-305.
Gee et al: "Shifting Gas Artefact Sign: Early Sonographic Detection of Pneumoperitoneum"; Emergency Medicine Australasia (1011), 23, pp. 647-650.
Grechenig et al: "Detection of Pneumoperitoneum by Ultrasound Examination:An Experimental and Clinical Study"; Injury, Int. J. Care Injured, (1999), pp. 173-178.
Hanbidge et al: "US of the Peritoneum"; Radiographics, 2003,23:663-685.
Hefny et al: "Sonographic Diagnosis of Intraperitoneal Free Air"; J. Emerg Trauma Shock, Oct.-Dec. 4, 2011 (4), pp. 511-513.
Hoffman et al: "Focus on Abnormal Air:Diagnostic Ultrasonography for the Acute Abdomen"; European Journal of Emergency Medicine, 2012, vol. 19(5)284-291.
Jones: "Recofnition of Pneumoperitoneum Using Bedside Ultrasound in Critically Ill Patients Presenting With Acute Abdominal Pain"; American Journal of Emergency Medicine, 2007, 25:838-841.
Karahan et al: "New Method for the Detection of Intraperitoneal Free Air by Sonography: Scissors Maneuver"; Journal of Clinical Ultrasound, vol. 32, No. 8, pp. 381-385.
Moore et al: "Point-of-Care Ultrasonography"; New England Journal of Medicine, 2011, vol. 364, pp. 749-757.
Moriwaki et al: "Ultrasonography for the Diagnosis of Intraperitoneal Free Air in Chest-Abdominal-Pelvic Blunt Trauma and Critical Acute Abominal Pain"; Arch Surg. 2009, vol. 144, No. 2, pp. 137-141.
Muradali et al: "A Specific Sign of Pneumoperitoneum on Sonography: Enhancement of the Peritoneal Stripe"; AJR:173, Nov. 1999, pp. 1257-1262.
Pattison et al: "Sonography of Intraabdominal Gas Collections"; AJR, 1997, vol. 169, pp. 1559-1564.
Wilkerson et al: "Sensitivity of Bedside Ultrasound and Supine Anteroposterior Chest Radiographs for the Identification of Pneumothorax After Blunt Trauma"; Academic Emergency Medicine 2010; vol. 17, pp. 11-17.
Wilson et al: "Gas at Abdominal US:Appearance, Relevance, and Analysis of Artifacts"; Radiology 1999, vol. 210, pp. 113-123.

* cited by examiner

METHOD AND APPARATUS FOR DETECTING A GAS POCKET USING ULTRASOUND

CROSS-REFERENCE TO PRIOR APPLICATIONS

This application is the U.S. National Phase application under 35 U.S.C. § 371 of International Application No. PCT/EP2015/050438, filed on Jan. 13, 2015, which claims the benefit of Chinese Patent Application No. PCT/CN2014/071839, filed on Jan. 30, 2014 and Chinese Patent Application No. PCT/CN2014/075396, filed on Apr. 15, 2014, and European Patent Application No. 14170204.3, filed on May 28, 2014. These applications are hereby incorporated by reference in their entirety herein.

FIELD OF THE INVENTION

The present invention relates to ultrasound imaging, particularly to a method and an apparatus for detecting a gas pocket using ultrasound.

BACKGROUND OF THE INVENTION

Trauma is the leading cause of death in the United States for men and women under the age of 45 years and the fourth overall cause of death for all ages. Trauma also has a substantial economic impact on the health care system, accounting for over one-third of all emergency department visits and resulting in over $80 billion per year in direct medical care cost, for example, in 2007, over 180 000 people died of trauma, and abdominal injuries contributed to a large number of these deaths.

Pneumoperitoneum is a condition in which a free gas pocket or tiny amount of free gas or air is trapped within the abdominal cavity but not contained in a hollow viscus. Identifying abnormal intra-abdominal gas pockets or collections may be critically important in establishing an accurate diagnosis. Increasing evidence supports that ultrasound imaging is a very useful tool for diagnosis of pneumoperitoneum with abnormal air/gas patterns because of its high accuracy and superiority as compared to plain X-ray radiography. The sonographic air can be outlined as comprising two categories: physiological air or normal air; and pathologic air or abnormal air. Physiological air is air in the gastrointestinal tract and lungs (air projecting into the abdominal cavity).

Bedside ultrasound or Point-of-care Ultrasound is widely used in emergency medicine for initial screening and enables selection of hemodynamically unstable traumatic patients with severe hemoperitoneum for immediate surgery. The detection of intraperitoneal free air or an intraperitoneal gas pocket is very helpful for bedside diagnosis of acute abdomen and trauma patients. The detection of a gas pocket may support doctors to assess, although not in a direct way, if there is an abnormal gas pocket from blunt abdominal trauma or from acute abdomen in (a) pre-hospital settings, (b) initial evaluation in the emergency room, and (c) follow-up after some treatments.

The sonographic appearance of gas pockets is due to total ultrasound reflection (a strong reflector) at the interface of soft tissue and gas pocket (air). This reflection is accompanied by reverberation of ultrasound between the gas pocket and the ultrasound probe. Therefore, sonographic images for gas pockets typically appear as high-amplitude echoes (brightness area in the image) with distal artifactual reverberation echoes referred to as "dirty shadowing"; small reverberation artifacts have a characteristic comet-tail appearance. Small gas pockets may show little or no distal reverberation artifacts with standard abdominal transducers. The optimal probe position for detecting intraperitoneal free air after blunt abdominal trauma is in the right paramedian epigastric area in the longitudinal direction.

Muradali et al. ("A specific sign of pneumoperitoneum on sonography: enhancement of the peritoneal stripe", AJR, 1999, Vol. 173:1257-1262) studied the signs of pneumoperitoneum from animal models, which were then confirmed in patients who had undergone laparoscopy. This kind of characteristics of gas pockets in the ultrasound images is called Enhancement of the Peritoneal Stripe Sign (EPSS). This EPSS is further confirmed by recent prospective study of six hundred consecutive patients with acute abdominal pain. The EPSS had a sensitivity of 100%, a specificity of 99%, a positive predictive value of 87.5% and a negative predictive value of 100%. Therefore, EPSS is recommended as a reliable and accurate sonographic sign for the diagnosis of pneumoperitoneum through visual observation.

Conventional gas pocket detection based on ultrasound imaging works well if gas pockets are quite large, i.e. large enough to produce enhancement of the peritoneal stripe sign (EPSS). It takes a long time for non-experienced users to identify this kind of sign (EPSS) from ultrasound images. It is really difficult for emergency physicians to identify all gas pockets in an examination time of around 5 minutes for the whole abdomen even if they know the optimal probe position for detecting intraperitoneal free air after blunt abdominal trauma in the right paramedian epigastric area in the longitudinal direction.

In summary, larger gas pockets may appear as bright, highly echogenic stripes or lines with distal reverberation and dirty shadowing artifacts or comet-tail artifacts which may even obscure the underlying abdominal organs. Smaller gas pockets can appear as bright punctuate foci without ring-down artifacts and shadowing within the intestinal lumen, but may not have reverberation within the image. Ultrasound imaging is superior to chest X-rays for diagnosing intraperitoneal free air; quantities as small as 1 ml to 2 ml of intraperitoneal free air can be detected by ultrasound. However, the detection of intraperitoneal free air might be difficult even for an experienced sonographer in emergency situations under difficult patient conditions.

Thus, most of the existing gas pocket detection approaches are based on visual observations of B-mode ultrasound images showing comparisons between normal soft tissue and gas pockets. Such existing approaches are time-consuming and the accuracy is very dependent on the operator's experience.

SUMMARY OF THE INVENTION

Therefore, it would be advantageous to provide an improved method and apparatus or system for detecting a gas pocket in a Region-of-Interest (ROI).

According to an embodiment of a first aspect of the present invention, there is proposed an ultrasound system for detecting a gas pocket. The ultrasound system comprises: an ultrasound probe for transmitting an ultrasound pulse toward the ROI and acquiring an ultrasound echo signal reflected from the ROI along a plurality of scanning lines; an obtaining unit for obtaining a second harmonic component of the ultrasound echo signal for each depth of a plurality of depths along each scanning line of the plurality of scanning lines; and a deriving unit for deriving a change in a center frequency of the second harmonic component along with the depth. The term "depth" refers to the penetration depth of the ultrasound signal. The term "scanning line" is also called "receiving line" in the field of ultrasound imaging.

The inventors of the present application recognize that the center frequency of the second harmonic component of the ultrasound echo signal is expected to decrease along the penetration depth at a certain rate in the area where the normal soft tissue is present, whilst it is expected to change in a different manner along the penetration depth in the area where the gas pocket is present. For instance, along the scanning line, the decrease of the center frequency of the second harmonic component (also referred to as the attenuation of the center frequency) due to the presence of the gas pocket at a specific depth is assumed to be greater than the decrease due to the presence of the soft issue at the same depth. Therefore, the inventors of the present application propose the aforementioned method. A person skilled in the art will appreciate that the term "area" is not intended to be restricted to a two-dimensional spatial region within the field of view of the ultrasound probe, and particularly, in case that the ultrasound probe is a 3D ultrasound probe for imaging a 3D ultrasound image, the term "area" can be understood as a two-dimensional or three-dimensional spatial region within the field of view of the ultrasound probe.

By means of the proposed method, the second harmonic component of the ultrasound echo signal reflected from the ROI is obtained and the change of the center frequency of the second harmonic component of the echo signal along with the depth is derived. Then, the gas pocket can be manually or automatically detected based on the derived change in the center frequency of the second harmonic component along with the depth. In particular, the change in the center frequency of the second harmonic component along with the depth can indicate the trend of the center frequency along with a plurality of depths (namely the trend along with the propagation or penetration direction of the ultrasound signal). In comparison with the decrease of the center frequency at a depth, the change in the center frequency of the second harmonic component reflects the trend of the decrease of the center frequency along with the depth and is expected to be more reliably used for detecting a gas pocket, especially a macro gas pocket.

According to an embodiment of a first aspect of the present invention, the second harmonic component is obtained by means of a pulse inversion technique.

It is appreciated by the person skilled the art that in the case of pulse inversion technique, two transmissions (i.e. one positive pulse transmission and one negative transmission) and two corresponding receptions are conducted for each scanning line. By using pulse inversion technique, the boundary of a possible gas pocket and dark areas behind the gas pocket may be clearly visible, and also the contrast between the boundary of different tissues is improved.

According to an embodiment of a first aspect of the present invention, the second harmonic component is obtained by means of band-pass filtering. It is appreciated by the person skilled in the art that in the case of using band-pass filtering (hereinafter referred to as band-pass filtering approach), the second harmonic component can be derived from one transmission and one corresponding reception along each scanning line. Thus, in comparison to the pulse inversion technique, the advantages of the band-pass filtering approach include an increased frame rate and/or less sensitivity to motion artifacts.

According to an embodiment of a first aspect of the present invention, the deriving unit is configured to derive, for each scanning line, a frequency-depth curve representing the relationship between the center frequency and the depth, and to derive the slope of the frequency-depth curve at each depth of the plurality of depths.

In other words, the frequency-depth curve represents the center frequency with respect to the depth, and hence its slope represents the rate of the change of the center frequency along with the depth.

According to an embodiment of a first aspect of the present invention, the frequency-depth curve is smoothened by averaging over a second predetermined number of ultrasound scanning lines. For example, the center frequency at a depth along a scanning line in the smoothened frequency-depth curve is computed as the moving average window (also known as the sliding average) with a size equal to the second predetermined number of scanning lines. Given a sequence of samples, the moving average of a sample is known to be defined as the average value of all samples within a window containing that sample.

By means of said smoothening over a number of ultrasound scanning lines, undesirable distortions caused by noises and/or disturbances can be reduced thanks to the averaging effect.

According to an embodiment, the ultrasound system further comprises a display unit for generating an ultrasound image representing the derived change in the center frequency along with the depth, and for displaying the ultrasound image.

In this way, users, such as doctors or sonographers, can obtain knowledge about the change of the center frequency along with the depth by viewing the ultrasound image, and judge whether there is a gas pocket based on the obtained knowledge. For example, if it is observed that the center frequency drops sharply along with the depths at a location, the users can infer that there is a high possibility that a gas pocket exists at that location.

According to an embodiment, the ultrasound system further comprises a detecting unit for detecting a gas pocket based on the change of the center frequency along with the depth, and a display unit for displaying, in an ultrasound image, an indicator for indicating the detected gas pocket.

In this way, the results of gas pocket detection are directly presented to the users. The indicator for the detected gas pocket can be displayed in various types of ultrasound images, such as a B-mode ultrasound image, an ultrasound image illustrating the change of the center frequency along with the depth, or a combination thereof.

According to an embodiment, the second harmonic component is obtained by means of pulse inversion technique, and the gas pocket is detected at a depth if an amount of the change in the center frequency along with the depth exceeds a first predetermined threshold at the depth. In other words, the gas pocket can be detected in the case of a sharply changed center frequency of the second harmonic component along with the depth, whereas soft tissue can be detected in the case of a nearly linearly changed center frequency of the second harmonic component along with the depth.

According to another embodiment, the second harmonic component is obtained by means of a band-pass filtering approach, and the detecting unit is configured to obtain a first determining result indicating whether the change in the center frequency along with the depth in an area forms a bell shape, and to determine whether a gas pocket is present in the area based on the first determining result. In other words, if a gas pocket is present in an area, the curve for the center frequency of the second harmonic component with respect to the depth is expected to increase initially at the gas-pocket boundary and then decrease sharply, which combination of generation and transmission process forms a bell-shape curve. The person skilled in the art will understand that the change of a parameter forms a bell shape if the parameter first increases and then decreases.

According to the understanding of the inventors of the present invention, the high frequency components of the produced echo signal including the second or higher order harmonic component will become stronger when the ultrasound signal hits the boundary of a gas pocket, and then decrease sharply along the depth due to the stronger attenuation caused by the same gas pocket.

According to another embodiment, the detecting unit is configured to determine whether a gas pocket is present between a first depth and a second depth along a scanning line based on a second determining result, wherein the second depth is deeper than the first depth, and the second determining result indicates, along the scanning line, whether the change in the center frequency along with the depth is greater than a non-negative second predetermined threshold at the first depth and less than a non-positive third predetermined threshold at the second depth. In an example, both the second predetermined threshold and the third predetermined threshold are zero. In this case, a gas pocket is detected if a positive slope is followed by a negative slope in a frequency-depth curve representing the relationship between center frequency of the second harmonic component and depth.

According to an embodiment, the detecting unit is configured to obtain a third determining result indicating whether the intensity of the ultrasound echo signal at the first depth is lower than a fourth threshold, and to determine whether a gas pocket is present between the first depth and the second depth based on the second determining result and the third determining result. In an example, the fourth threshold is determined based on the average intensity of the ultrasound echo signal in the whole ROI. If the ultrasound echo signal in an area is far below the average intensity in the whole ROI, the derived change of the center frequency of the second harmonic component along with the depth may be so contaminated by noise and/or artifacts that the detecting based thereon is not reliable anymore. Thus, the detection accuracy can be improved if detecting the gas pocket is further based on the intensity of the ultrasound echo signal. In various embodiments, the intensity of the ultrasound echo signal can be represented by the intensity of the fundamental component, or the second harmonic component, or the frequency component of the ultrasound echo signal.

According to an embodiment of a second aspect of the present invention, there is proposed a method of detecting a gas pocket. The method comprises: transmitting an ultrasound signal toward the ROI and acquiring an ultrasound echo signal reflected from the ROI along a plurality of scanning lines; obtaining a second harmonic component of the ultrasound echo signal for each depth of a plurality of depths along each scanning line of the plurality of scanning lines; and deriving a change in a center frequency of the second harmonic component along with the depth.

Other objects and advantages of the present invention will become more apparent and can be easily understood with reference to the description made in combination with the accompanying drawings.

DESCRIPTION OF THE DRAWINGS

The present invention will be described and explained hereinafter in more detail in combination with embodiments and with reference to the drawings, wherein.

Figure 1:
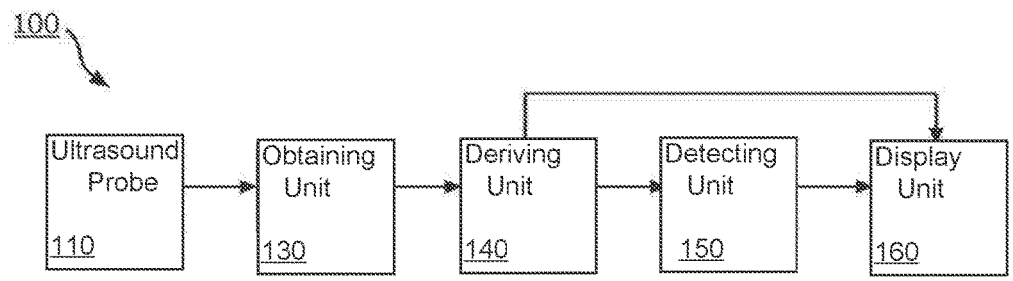
FIG. 1 is a schematic diagram of an ultrasound system for detecting a gas pocket in accordance with an embodiment of the present invention.

The same reference signs in the figures indicate similar or corresponding features and/or functionalities.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

FIG. 1 shows a schematic diagram of an ultrasound system 100 for detecting a gas pocket in a Region-of-Interest (ROI) in accordance with an embodiment of the present invention. As shown in FIG. 1, the ultrasound system 100 includes an ultrasound probe 110 for transmitting an ultrasound signal toward the ROI and acquiring an ultrasound echo signal reflected from the ROI. The ultrasound echo signal may be pre-processed to reduce noise and/or motion artifacts.

The pre-processed signals are coupled to an obtaining unit 130. The obtaining unit 130 is configured to obtain a second harmonic component of the ultrasound echo signal for each depth of a plurality of depths on a scanning line in the ROI.

According to an embodiment of a first aspect of the present invention, the second harmonic component is obtained by means of a pulse inversion technique. As known by the person skilled in the art, positive pulse transmission and negative pulse transmission are successively performed along with each scanning line, and two corresponding RF (radio frequency) lines are received, respectively. The pulse inversion version of the ultrasound echo signal is the sum of the two RF lines, namely the sum of the received echo of the positive pulse transmission and the received echo of the negative pulse transmission. Generally, when the ultrasound signal encounters a gas pocket, it alternately compresses the gas pocket in the positive pressure phase and expands it in the negative pressure phase. However, the extent to which the gas pockets are compressed during the positive pressure phase does not correspond to the extent of expansion in the negative pressure phase. In other words, the compression and expansion are not symmetrical and thus harmonic components are produced.

In an exemplary embodiment, the received ultrasound echo signal comprises a raw 512-line RF signal collected along 256 scanning lines in tissue harmonic mode, 256 lines of which are the echoes of the positive pulse transmission and the other 256 lines of which are the echoes of the negative pulse transmission. Then, a new 256-line RF signal indicating the pulse inversion version is derived from the raw 512-line RF signal. The new 256-line RF signal is then pre-processed to reduce noise or motion artifacts.

Figure 2:
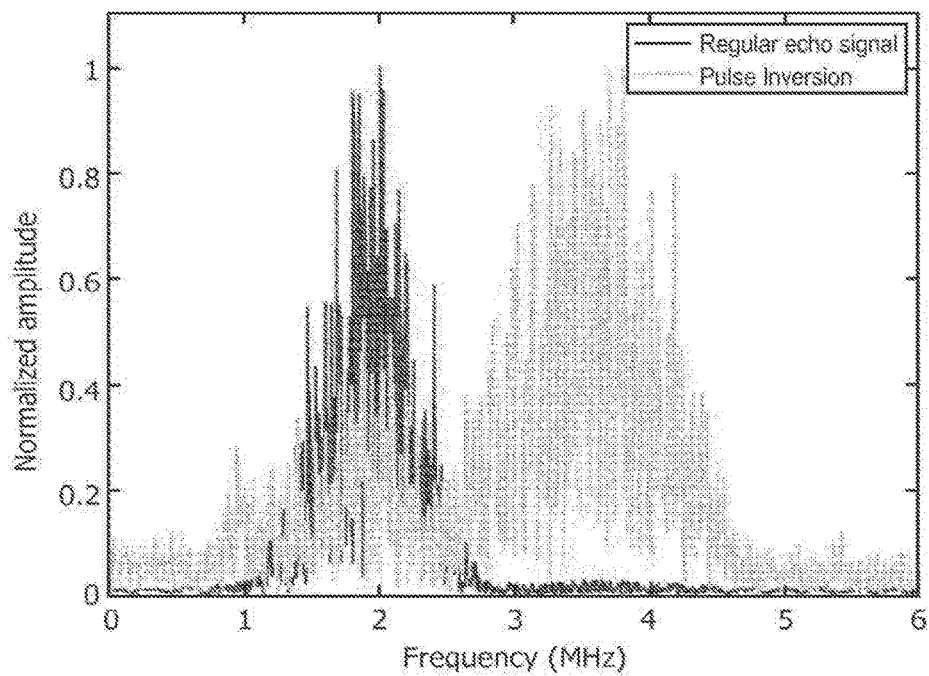
FIG. 2 shows the respective normalized spectra for a regular ultrasound echo signal and its pulse inversion version.

FIG. 2 shows the respective normalized spectra for a regular ultrasound echo signal and its pulse inversion version. It can be seen that the energy of the second harmonic component obtained from the pulse inversion at a bandwidth of [2.5 to 5] MHz is around 70% to 80% of the total energy from the pulse inversion signal. Therefore, the second harmonic component can be generally selected as the bandwidth for spectral analysis.

Harmonic imaging relies on transmitting at a fundamental frequency and forming an image from harmonic components of the ultrasound echo signal, where filters are used to remove the fundamental component. Pulse inversion technique can separate the fundamental component of the gas pocket echoes from the harmonic components even when they overlap. In pulse inversion technique, any linear target (e.g., tissue) that responds equally to positive and negative pressures will reflect equally and its respective echo signals will cancel out.

Gas pockets respond differently to positive and negative pressures and do not reflect identical inverted waveforms. When these echo signals are added, they do not cancel out completely. By using the pulse inversion technique, the boundary of possible gas pockets and dark areas behind the gas pockets becomes clearly visible and also the boundary of different tissue exhibits better contrast. By comparison, conventional B-scan images do not show dark areas behind a gas pocket very clearly. As such, a B-scan image from pulse inversion (major second harmonic component) shows better contrast than that from conventional ultrasound. As such, for further non-linear analysis, the second harmonic component mentioned above may be obtained by means of pulse inversion technique.

Examples of signals used for further non-linear analysis are not limited to second harmonic components obtained by means of pulse inversion technique. For example, regular second harmonic components can also be selected for non-linear analysis.

According to another embodiment, the second harmonic component is obtained by means of a band-pass filtering approach. In particular, the obtaining unit 130 comprises a band-pass filter. Alternatively, the obtaining unit 130 can comprise a low-pass filter and a high-pass filter.

As known by the skilled person, fundamental component, second harmonics and even higher order harmonics (if the bandwidth of the ultrasound probe is wide enough to have higher order harmonics) are all present in the ultrasound echo signal, and there is spectrum overlapping between fundamental component and 2nd harmonics as well as between second harmonics and higher order harmonics.

In an embodiment, the ultrasound echo signal along each scanning line is collected and then a band-pass digital filter with a lower cut-off frequency f1 and an upper cut-off frequency f2 is applied to obtain the second harmonic component of the ultrasound echo signal. Alternative to a band-pass digital filter, a high-pass digital filter with the lower cut-off frequency f1 and a low-pass digital filter with the upper cut-off frequency f2 can be applied. The lower cut-off frequency and the upper cut-off frequency can be predetermined based on the central frequency of the ultrasound signal. In an example, the central frequency of the ultrasound signal transmitted by the ultrasound probe is 2 MHz, and hence the central frequency of the second harmonic component is around 4 MHz. Thus, the lower cut-off frequency f1 can be set in the range from 2.7 MHz to 3.2 MHz, preferably at 3.0 MHz, and the upper cut-off frequency f2 can be set in the range from 5.0 MHz to 5.5 MHz, preferably at 5.0 MHz.

In an exemplary embodiment, a raw 512-line RF signal is collected along 256 scanning lines in tissue harmonic mode, 256 lines of which are the echoes of the positive pulse transmission and the other 256 lines of which are the echoes of the negative pulse transmission. Either the 256 lines of the positive pulse transmission or the 256 lines of the negative pulse transmission are selected, referred to as a new 256-line RF signal. The new 256-line RF signal is then pre-processed to reduce noise and/or motion artifacts. Thereafter, the obtaining unit 130 obtains the second harmonic component from the pre-processed new 256-line RF signal.

Referring back to FIG. 1, the obtained second harmonic component, for example the pulse inversion version of the ultrasound echo signal, is coupled to a deriving unit 140. The deriving unit 140 is configured to derive a change in a center frequency of the second harmonic component along with the depth.

The obtaining unit 130 and the deriving unit 140 can be implemented as a single processor or separate processors.

An ultrasound system normally comprises one or more processors such as a signal processor coupled to a beam former and a B mode processor coupled to the signal processor. The signal processor can process the received echo signals in various ways, such as bandpass filtering, decimation, I and Q component separation, and harmonic signal separation which is applied to separate linear and nonlinear signals so as to enable identification of nonlinear (higher harmonics of the fundamental frequency) echo signals returned from tissue and microbubbles. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information. The processed signals are coupled to the B mode processor. The B mode processor employs detection of an amplitude of the received ultrasound signal for the imaging of structures in the body such as the tissue of organs and vessels in the body. B mode images of structures of the body may be formed in either the harmonic image mode or the fundamental image mode or a combination of both, as described in U.S. Pat. No. 6,283,919 (Roundhill et al.) and U.S. Pat. No. 6,458,083 (Jago et al.). In various embodiments, the obtaining unit 130 or the deriving unit 140 can be implemented as part of the existing one or more processors, or as a separate processor.

In order to derive the change in center frequency of the second harmonic component along with the depth, the center frequency of the second harmonic component at a depth along each scanning line is derived. As known by the skilled person, the center frequency of the second harmonic component can be derived, for example, in the following way. The power spectrum of the second harmonic component is derived using a sliding window having a first predetermined number of samples. The first predetermined number of samples can range from 50 to 500 samples. Preferably, the first predetermined number of samples is 150, i.e. the sliding window can have a size of 150 samples. In an example, the sliding window may move 2 samples at a time. The power spectrum of the second harmonic component at each depth can be computed based on the first predetermined number of samples, for example by using a 4096 or 8192-point FFT (adding zeros after the first predetermined number of samples). In an example, the power spectrum can be averaged over a number of RF lines, such as three RF lines, by means of "sliding average". Thereafter, the center frequency of the second harmonic component is computed from the power spectrum. For example, from the power spectrum $P_{l,d}(f)$ at the d-th depth along the l-th scanning line, the center frequency $f_{l,d}^{center}$ at d-th depth along the l-th scanning line is computed as:

$$f_{l,d}^{center} = \frac{\int_f f \cdot P_{l,d}(f)df}{\int_f P_{l,d}(f)df}$$

Since the attenuation/decrease of the center frequency due to a gas pocket at a specific depth is assumed to be greater than that due to soft issue at the same depth, the change in the center frequency of the second harmonic component along with the depth can be used for indicating the existence of a gas pocket. For example, a gas pocket might be detected in case of a sharply changed center frequency of the second harmonic component along with the depth, whereas soft tissue might be detected in case of a nearly linearly changed center frequency of the second harmonic component along with the depth.

In an aspect, a frequency-depth curve for the scanning line of the plurality of scanning lines in the ROI can be derived by determining the center frequency of the second harmonic component for each depth of the scanning line. Such frequency-depth curve for the scanning line can represent the relationship between the center frequency of the second harmonic component and the depth and thus represent the change of the center frequency of the second harmonic component along with the depth.

Similarly, another frequency-depth curve for another scanning line of the plurality of scanning lines in the ROI can also be derived, and so on. As a result, for each scanning line of the plurality of scanning lines in the ROI, a respective frequency-depth curve can be derived. As such, the frequency-depth map for the ROI can be established based on all or a portion of the frequency-depth curves for the plurality of scanning lines in the ROI.

According to an embodiment of the present invention, the frequency-depth curve or map can be smoothened by averaging over a second predetermined number of scanning lines. For example, a smooth function such as a moving average function (also called sliding average function) can be applied. Preferably, the second predetermined number ranges between 2 and 50 lines. For example, the second predetermined number of scanning lines can be selected to be 50 lines.

Figure 3A:
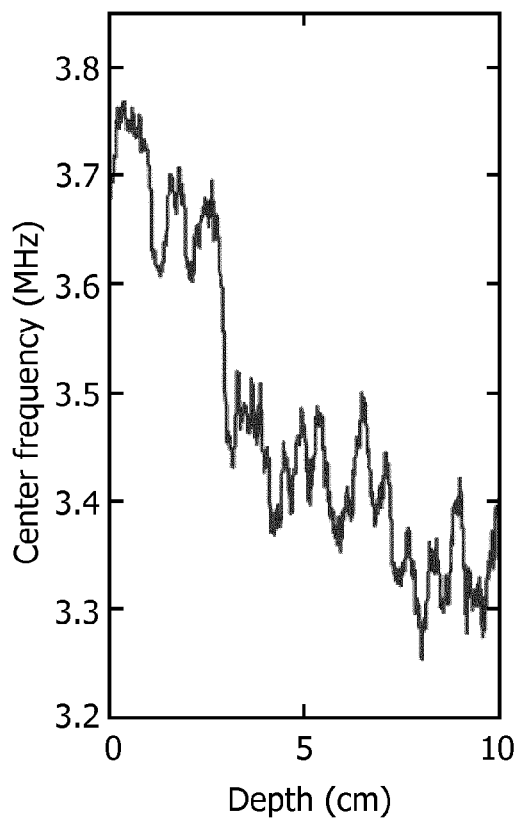
FIG. 3a and FIG. 3b show typical frequency-depth curves for a gas pocket and normal soft tissue (liver)
Figure 3B:
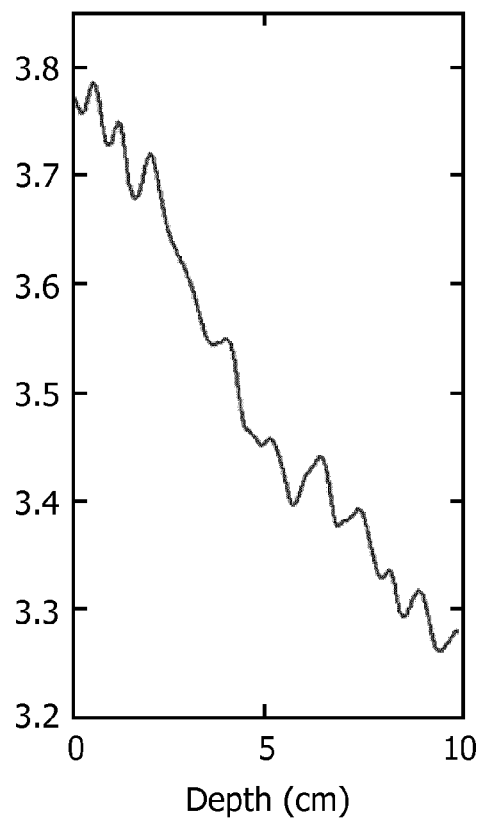

Two typical frequency-depth curves are shown in FIG. 3a and FIG. 3b, where the relationship between center frequency of the second harmonic component and depth can be represented by such frequency-depth curve. In the examples of FIG. 3a and FIG. 3b, the second harmonic component is obtained by means of pulse inversion technique.

Referring back to FIG. 1, the deriving unit 140 is coupled to a detecting unit 150. The detecting unit 150 is configured to detect a gas pocket based on the change of the center frequency of the second harmonic component in the depth direction. The obtaining unit 130, the deriving unit 140 and the detecting unit 150 can be implemented as a single processor or separate processors.

A display unit 160 is coupled to the deriving unit 140. The display unit 160 is configured to generate an ultrasound image representing the derived change in the center frequency of the second harmonic component along with the depth.

Additionally or alternatively, the display unit 160 is coupled to the detecting unit 150 and is configured to display, in an ultrasound image, an indicator for indicating the detected gas pocket. The ultrasound image can be of various types, such as a B-mode ultrasound image, an ultrasound image representing the change of the center frequency along with the depth, or a combination thereof. The B-mode ultrasound image may represent the short-time energy of the echo signal or the short-time energy of the second harmonic component of the echo signal. The short-time energy may be derived using a sliding window. The size of the sliding window may range from 50 to 500 samples. For example, the sliding window can have a size of 150 samples and move 2 samples at a time.

The detecting unit 150 can be configured to detect the gas pocket in various ways.

In an embodiment, in the case that the second harmonic component is obtained by means of pulse inversion technique, the detecting unit 150 is configured to detect a gas pocket in the following way. If, in the depth direction, the amount of change of the center frequency of the second harmonic component at a depth exceeds a first predetermined threshold, it is detected that there is a gas pocket at said depth.

Referring again to FIG. 3a and FIG. 3b, the relationship between center frequency of the second harmonic component and depth can be represented by each of the two frequency-depth curve. In an aspect, the change in center frequency along with depth can be reflected by a slope of the frequency-depth curve at a respective depth. We note that in FIG. 3a the center frequency drops sharply at a depth around 2.3 cm to 3.0 cm; while in FIG. 3b the center frequency decreases nearly linearly along with the depth.

Through analyzing data sets, the acoustical characteristics of a gas pocket and normal soft tissue can be determined through analysis of ultrasound echo signals. In one aspect, a sharp drop of the average frequency along with depth may be considered as being caused by a gas pocket. In another aspect, a nearly linearly average frequency along with depth may be considered as being caused by normal soft tissues. For example, in FIG. 3a and FIG. 3b, the frequency-depth curve in FIG. 3a may relate to a gas pocket, and the frequency-depth curve in FIG. 3b may relate to normal soft tissue (liver).

As described above, the gas pocket can be detected by comparing the amount of change in the center frequency of the second harmonic component along with depth with a first predetermined threshold. If the amount of change at a depth exceeds the first predetermined threshold in an area, the area possibly contains a gas pocket; otherwise, the area possibly contains soft tissues. The first predetermined threshold can be experimentally derived. For example, the first predetermined threshold can be derived by performing a statistical analysis on the slopes of the aforementioned frequency-depth curve for the presence of a gas pocket and normal soft tissue. The absolution value of the slopes represents the amount of change of the center frequency of the second harmonic component.

A parametric slope map for the ROI can be generated to represent the slopes at the plurality of depths of the smoothened frequency-depth curve for each scanning line. The slope values can be for example in MHz per cm. In an embodiment, the parametric slope map can be colorized to obtain a colorized parametric slope map, in which the slope value is represented by a color. A color bar is often provided adjacent to each colorized parametric map to indicate the correspondence between the colors and the values indicated by the colors. Typically, the colorized parametric map is colorized with various colors. As a particular example, the parametric map can be colorized by various grey levels.

Figure 4A:
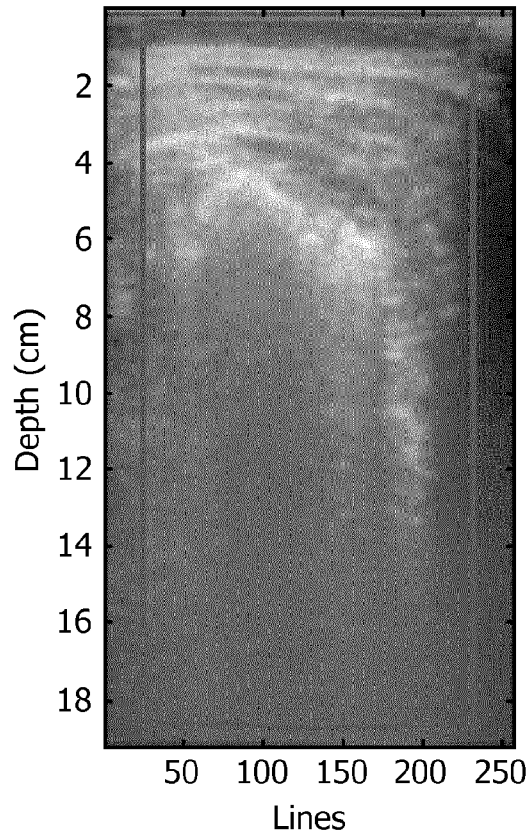
FIG. 4a shows a grey B-mode ultrasound image of a region of interest (ROI)
Figure 4B:
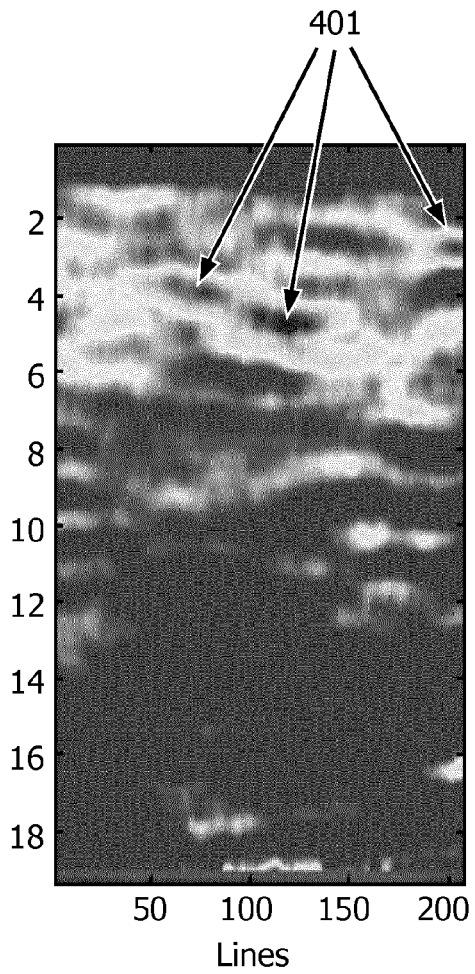
FIG. 4b shows a colorized parametric ultrasound image of the ROI.
Figure 4C:
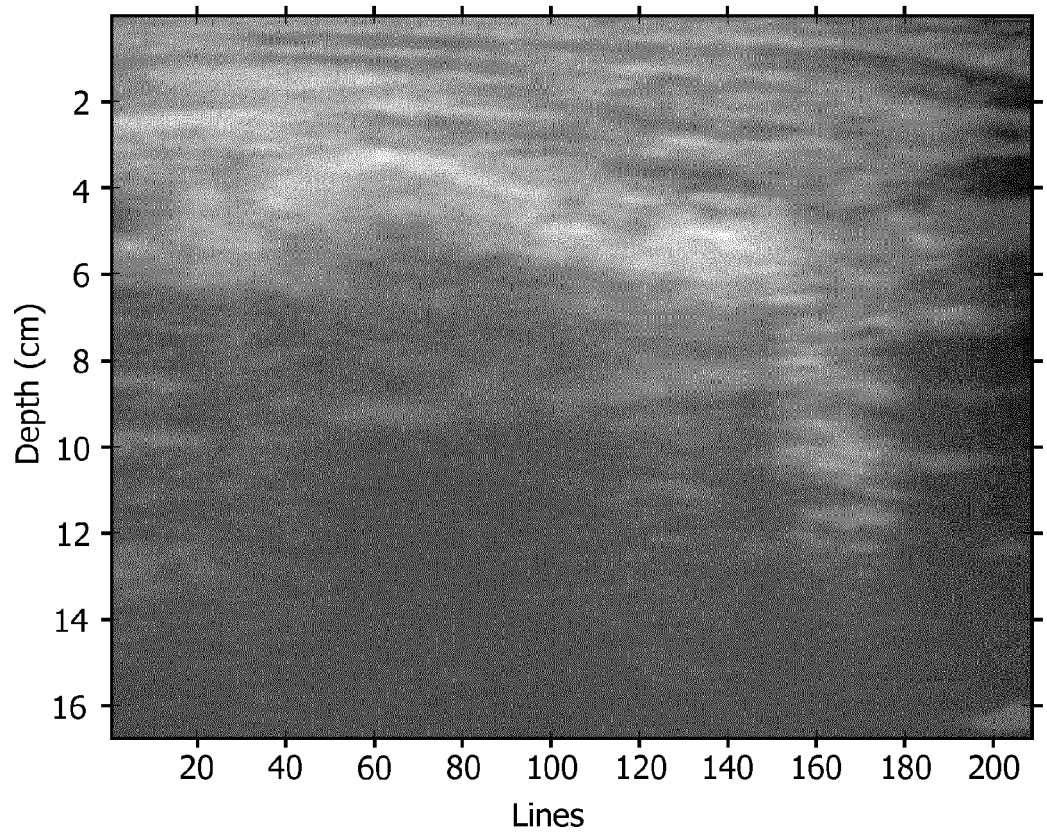
FIG. 4c shows the colorized parametric ultrasound image overlaid with the grey B-mode ultrasound image.

FIG. 4a shows a grey B-mode ultrasound image of a region of interest (ROI), FIG. 4b shows a colorized parametric ultrasound image of the ROI, and FIG. 4c shows the colorized parametric ultrasound image overlaid with the grey B-mode ultrasound image. The colorized parametric ultrasound image represents the colorized parametric slope map as described above. Dynamic ranges for grey B-scan image and color map are 60 dB and 0.3, respectively. In the example of FIGS. 4a-4c, the second harmonic component is obtained by means of pulse inversion technique.

Referring to FIG. 4b, the blue color represents a smaller slope (i.e. the absolution value of the slope is higher) and thus a sharp drop of the center frequency of the second harmonic component, whilst the red color represents a higher slope. Since the sharp drop of the center frequency indicates that a gas pocket could exist, the blue areas (such as areas 401) in FIG. 4b illustrate the locations of the possible gas pockets.

Referring to FIG. 4c, it shows the colorized parametric ultrasound image overlaid with the grey B-mode ultrasound image. Such an overlaid ultrasound image allows the users to detect the gas pocket using both the proposed approach based on the change of the center frequency of the second component and the conventional approach based on the B-mode ultrasound image, resulting in a more robust detection.

In some cases, the absolute value of the slope at a tissue boundary can be also very high, just like at a gas pocket. As is well-known, in the B-mode ultrasound image, the tissue boundary is normally darker or has a lower amplitude, whilst the gas pocket is normally brighter or has a higher amplitude. Through double checking the brightness and/or the amplitude in the B-mode ultrasound image, the gas pocket can be distinguished from the tissue boundary. In other words, the gas pocket may be brighter or has a higher amplitude than the tissue boundary.

In another embodiment, in the case that the second harmonic component is obtained by means of a band-pass filtering approach, the detecting unit 150 is configured to obtain a first determining result indicating whether the change in the center frequency along with the depth in an area forms a bell shape, and to determine whether a gas pocket is present in the area based on the first determining result. For example, if the center frequency of the second harmonic component in the middle of the area is higher than that in the other part of the area, it is determined that, in the area, the change of the center frequency along with the depth forms a bell shape. It will be appreciated by the skilled person that the first determining result, namely whether the change in the center frequency along with the depth in an area forms a bell shape, can be obtained in various ways such as by means of any suitable pattern recognition methods.

Additionally or alternatively, the detecting unit 150 is configured to determine whether a gas pocket is present between a first depth and a second depth along a scanning line based on a second determining result, wherein the second depth is deeper than the first depth, and the second determining result indicates, along the scanning line, whether the change in the center frequency along with the depth is greater than a positive second predetermined threshold at the first depth and less than a negative third predetermined threshold at the second depth. In an embodiment, the change in the center frequency along with the depth is represented by the slope of the frequency-depth curve. The skilled person in the art will appreciate that more than one scanning line may go across the same gas pocket, and the determined first and second depth along each of multiple adjacent scanning lines can be used to determine the outline of the gas pocket.

Experimental results show that the slope in the area of gas pocket is obviously larger than the slope in the area of surrounding normal soft tissue. Therefore, the area of a gas pocket and the area of surrounding normal soft tissue can be well differentiated based on the slope of the frequency-depth curve, for example, by comparing the slope with the corresponding predetermined thresholds.

In another embodiment, the detecting unit 150 is configured to obtain a third determining result indicating whether the intensity of the ultrasound echo signal at the first depth is lower than a fourth threshold, and to determine whether a gas pocket is present between the first depth and the second depth based on the second determining result and the third determining result. Preferably, the fourth threshold is determined based on the average intensity over the whole ROI. The intensity of the ultrasound echo signal can be, for example, represented by the short-time energy of the ultrasound echo signal, such as the image value of a regular B-mode image.

In particular, if the second determining result indicates there might be a gas pocket, but the third determining result indicates that the intensity of the ultrasound echo signal at the first depth is lower than the fourth threshold, the detecting unit 150 is configured so as not to determine there is a gas pocket.

In this way, the detecting accuracy can be improved for the following considerations. If the averaged intensity in an area after a positive slope is too low as compared to the averaged intensity in the whole image, said area is expected to be a near-field area associated with skin and fat, or a boundary, or there is too much noise or too many artifacts.

Figures 5A, 5B:
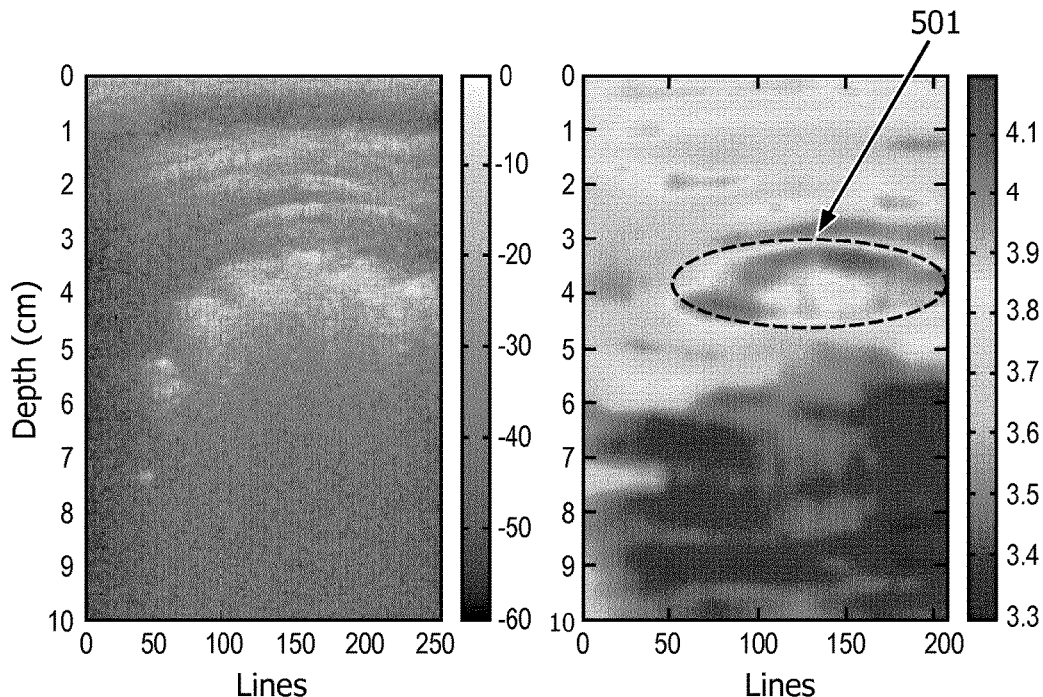
FIG. 5a shows a grey B-mode ultrasound image of a region of interest (ROI)
FIG. 5b shows one colorized parametric ultrasound image of the ROI representing the center frequency of the second harmonic component.
Figure 5C:
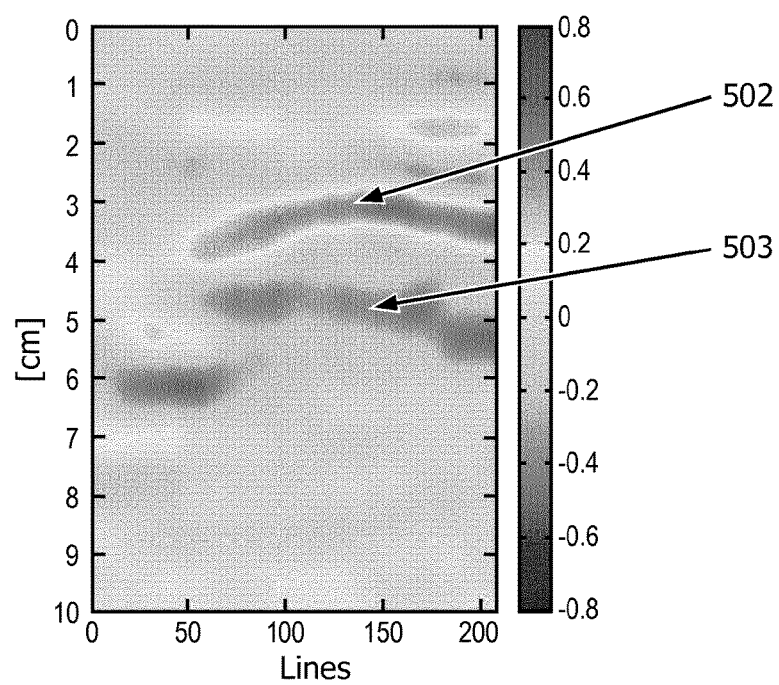
FIG. 5c shows another colorized parametric ultrasound image of the ROI representing the slope of the center frequency of the second harmonic component.
Figure 5D:
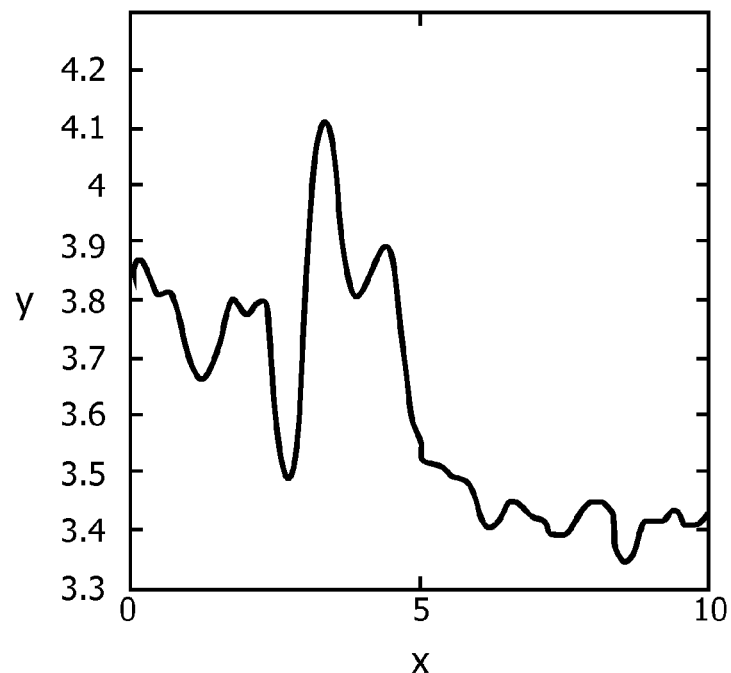
FIG. 5d shows the frequency-depth curve along the $150^{th}$ line in the ultrasound image of FIG. 5b.
Figure 5E:
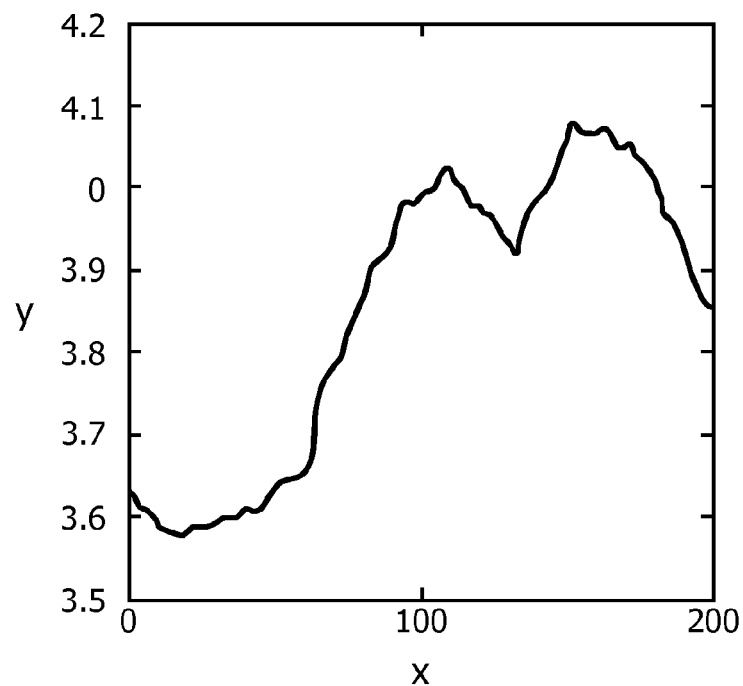
FIG. 5e shows the frequency-depth curve at a depth of 4 cm in the ultrasound image of FIG. 5b.

FIGS. 5a-5e shows an example in which the ultrasound echo signal is collected along 256 scanning lines in a region of interest (ROI), and the second harmonic component of the ultrasound echo signal is obtained by means of band-pass filtering. FIG. 5a shows a grey B-mode ultrasound image of the ROI, FIG. 5b shows one colorized parametric ultrasound image of the ROI representing the center frequency of the second harmonic component, FIG. 5c shows another colorized parametric ultrasound image of the ROI representing the slope of the center frequency of the second harmonic component, FIG. 5d shows the frequency-depth curve along the $150^{th}$ scanning line in the ultrasound image of FIG. 5b, and FIG. 5e shows the frequency-depth curve at a depth of 4 cm in the ultrasound image of FIG. 5b.

Referring to FIG. 5b, the x-axis represents the indices of the scanning line, the y-axis represents the depth in cm, and the color represents the center frequency of the second harmonic component of the ultrasound echo signal received from the ROI in MHz, as indicated by the color bar at one side. It can be seen from FIG. 5b that the center frequency generally decreases along with the depth, but there is an increase followed by a further decrease in area 501 and thereby a bell shape is formed in area 501. As described in the above, based on such a bell shape, it can be determined either manually (e.g. by a clinician's observation) or automatically (e.g. by the detecting unit 150) that a gas pocket is present in area 501. FIG. 5d shows the frequency-depth curve along the 150th scanning line in the ultrasound image of FIG. 5b. It can be clearly observed in FIG. 5d that the frequency-depth curve forms a bell shape approximately between 3.5 cm and 5 cm.

Referring to FIG. 5c, the x-axis represents the indices of the scanning line, the y-axis represents the depth in cm, and the color represents the slope of the center frequency of the second harmonic component along each scanning line, as indicated by the color bar at one side. It can be seen from FIG. 5c that the slope is generally in the range of [−0.2, 0.2] in the whole ROI, but the slope is approximately 0.5 at around 3.5 cm (as indicated by reference sign 502) and is approximately −0.5 at about 5 cm (as indicated by reference sign 503). As described in the above, based on such information, it can be determined either manually (e.g. by the clinician's observation) or automatically (e.g. by the detecting unit 150) that a gas pocket is present approximately between 3.5 cm and 5 cm.

Figure 6:
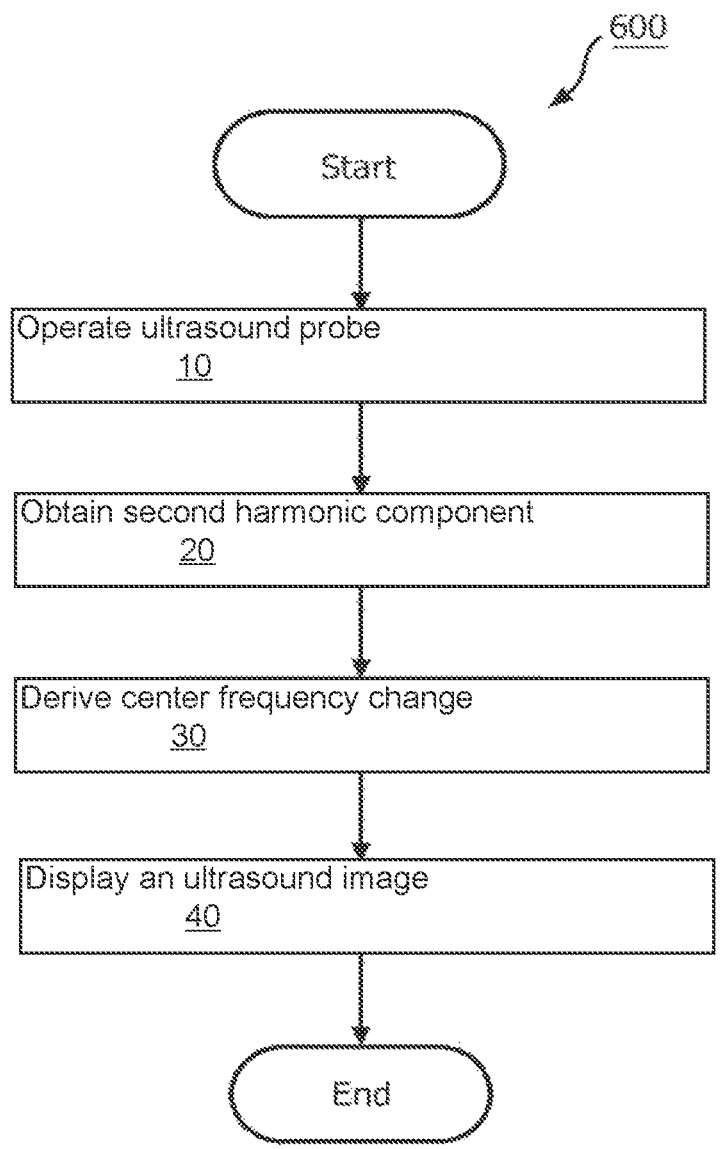
FIG. 6 shows a flowchart for an exemplary method of detecting a gas pocket.

Referring now to FIG. 6, a method 600 of detecting a gas pocket in the ROI is illustrated. While, for the sake of simplicity of explanation, the method is shown and described as a series of steps, it is to be understood and appreciated that the methodology is not limited by the order of steps, as some steps may occur, in accordance with one or more aspects, in different orders and/or concurrently with other steps as compared to the orders and steps shown and described herein. For example, those skilled in the art will understand and appreciate that a methodology could alternatively be represented as a series of interrelated states or events, such as in a state diagram. Moreover, not all illustrated steps may be utilized to implement a method in accordance with the claimed subject matter. In general, a process can be implemented as processor instructions, logical programming functions, or other electronic sequence that supports the detecting of gas pockets described herein.

FIG. 6 is an example gas pocket detection method 600 for an ultrasound system. The method 600 comprises step 10, step 20, step 30 and step 40.

At step 10, an ultrasound probe 110 is operated to transmit an ultrasound signal toward the ROI and to acquire an ultrasound echo signal reflected from the ROI along a plurality of scanning lines.

At step 20, a second harmonic component of the ultrasound echo signal may be obtained for each depth of a plurality of depths along each of the plurality of scanning lines. In an aspect, the second harmonic component is obtained by means of pulse inversion technique.

At step 30, a change of the center frequency of the second harmonic component along with the depth is derived, wherein the change in the center frequency of the second harmonic component along with the depth can be used to indicate the existence of a gas pocket. For example, a gas pocket might be detected in case of a sharply changed center frequency of the second harmonic component along with the depth, whereas soft tissue might be detected in case of a nearly linearly changed center frequency of the second harmonic component along with the depth.

In an aspect, step 30 comprises deriving, for each scanning line, a frequency-depth curve representing the relationship between the center frequency of the second harmonic component and the depth and deriving the slope of the frequency-depth curve at each depth. According to one example, the frequency-depth curve is smoothened by averaging over a second predetermined number of ultrasound scanning lines.

In another aspect, method 600 further comprises a step of detecting a gas pocket based on the change in the center frequency along with the depth. In an example, if an amount of the change in the center frequency along with the depth exceeds, at a depth, a first predetermined threshold, the gas pocket is detected at said depth. In another example, if the change in the center frequency along with the depth forms a bell shape in an area, it is detected that a gas pocket is present in the area.

Additionally, whether the detected gas pocket is normal or abnormal can be further determined based on the detected gas pocket and further information.

In an aspect, the further information may relate to the location of the gas pocket and to what type of tissue it is surrounded by. For example, a gas pocket surrounded by a liver-like texture might be abnormal since such a gas pocket is not expected to be seen there. According to another example, if the surrounding tissue of a gas pocket has a bowel-like appearance, then the gas pocket might be normal. According to yet another example, if the surrounding tissue of a gas pocket is not bowel-like, then, in general, the gas pocket might be abnormal.

At step 40, an ultrasound image is displayed.

In an embodiment, at step 40, an ultrasound image is generated based on the derived change in the center frequency of the second harmonic component along with the depth and then displayed. For example, the ultrasound image can be a colorized parametric ultrasound image as shown in FIG. 4b or FIG. 5c. In another embodiment, at step 40, an ultrasound image is generated, based on the center frequency of the second harmonic component along with the depth, and then displayed. For example, the ultrasound image can be a colorized parametric ultrasound image as shown in FIG. 5b.

Additionally or alternatively, at step 40, an indicator for indicating the detected gas pocket is displayed in an ultrasound image which may be of various types, such as a B-mode ultrasound image, an ultrasound image illustrating the change of the center frequency along with the depth, or a combination thereof. For example, the ultrasound image can be a grey B-mode ultrasound image as shown in FIG. 4a or FIG. 5a, a colorized parametric ultrasound image as shown in FIG. 4b or FIG. 5b or FIG. 5c, or the colorized parametric ultrasound image overlaid with the grey B-mode ultrasound image as shown in FIG. 4c.

The technique processes described herein may be implemented by various means. For example, these techniques may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. With software, implementation can be through modules (e.g., procedures, functions, and so on) that perform the functions described herein. The software codes may be stored in a memory unit and executed by the processors.

Moreover, aspects of the claimed subject matter may be implemented as a method, apparatus, system, or article of manufacture using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope or spirit of what is described herein.

As used in this application, the term "unit" such as "obtaining unit", "deriving unit", "detecting unit" is intended to refer to a processor or a computer-related entity, either hardware, a combination of hardware and software, software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. An ultrasound system comprising:
   an ultrasound probe configured to transmit an ultrasound signal toward a Region-of-Interest and acquire an ultrasound echo signal reflected from the Region-of-Interest along a plurality of scanning lines;
   an obtaining unit configured to receive the ultrasound echo signal and to obtain a second harmonic component of the ultrasound echo signal for each depth of a plurality of depths along each scanning line of the plurality of scanning lines;
   a deriving unit configured to:
      receive the second harmonic component;
      derive a change in a center frequency of the second harmonic component at the plurality of depths; and
   a detecting unit configured to:
      receive the derived change in the center frequency of the second harmonic component at the plurality of depths; and
      detect a gas pocket based on the change in the center frequency at a depth of the plurality of depths, wherein the gas pocket is detected at the depth if an amount of the change in the center frequency at the depth exceeds a first predetermined threshold at the depth; and
   a display unit coupled to the detecting unit and configured to display, in an ultrasound image, an indicator for indicating the detected gas pocket.

2. The ultrasound system according to claim 1, wherein the second harmonic component is obtained by means of pulse inversion technique.

3. The ultrasound system according to claim 1, wherein the second harmonic component is obtained by means of band-pass filtering.

4. The ultrasound system according to claim 1, wherein the deriving unit is configured
   to derive, for each scanning line, a frequency-depth curve representing the relationship between the center frequency and the depth; and
   to derive a slope of the frequency-depth curve at each depth of the plurality of depths.

5. The ultrasound system according to claim 4, wherein the frequency-depth curve is smoothened by averaging over a second predetermined number of ultrasound scanning lines.

6. The ultrasound system according to claim 1, further comprising:
   a display unit configured to generate an ultrasound image representing the derived change in the center frequency along with the depth and displaying the ultrasound image.

7. The ultrasound system according to claim 1, wherein the second harmonic component is obtained by means of pulse inversion technique.

8. The ultrasound system according to claim 1, wherein the second harmonic component is obtained by means of band-pass filtering; and
   the detecting unit is configured to obtain a first determining result indicating whether the change in the center frequency along with the depth in an area forms a bell shape, and to determine whether a gas pocket is present in the area based on the first determining result.

9. The ultrasound system according to claim 1, wherein the second harmonic component is obtained by means of band-pass filtering; and
   the detecting unit is configured to determine whether a gas pocket is present between a first depth and a second depth along a scanning line based on a second determining result, wherein the second depth is deeper than the first depth, and the second determining result indicates, along the scanning line, whether the change of the center frequency along with the depth is greater than a positive second predetermined threshold at the first depth and less than a negative third predetermined threshold at the second depth.

10. The ultrasound system according to claim 9, wherein the detecting unit is configured to obtain a third determining result indicating whether the intensity of the ultrasound echo signal at the first depth is lower than a fourth threshold, and to determine whether a gas pocket is present between the first depth and the second depth along the scanning line based on the second determining result and the third determining result.

11. The ultrasound system according to claim 1, further comprising: a determining unit configured to determine if the detected gas pocket is normal or abnormal based on the detected gas pocket and further information, wherein the further information relates to location of the gas pocket and information on what type of tissue surrounds the gas pocket.

12. A method of detecting a gas pocket in a Region-of-Interest, comprising steps of:
- transmitting, by an ultrasound probe, an ultrasound signal toward the Region-of-Interest and acquiring, by the ultrasound probe, an ultrasound echo signal reflected from the Region-of-Interest along a plurality of scanning lines;
- obtaining, by an obtaining unit, a second harmonic component of the acquired ultrasound echo signal for each depth of a plurality of depths along each scanning line of the plurality of scanning lines; and
- deriving, by a deriving unit, a change in a center frequency of the obtained second harmonic component at the plurality of depths;
- detecting, by a detecting unit, a gas pocket at a depth of the plurality of depths at which an amount of the derived change in the center frequency exceeds a threshold at the depth;
- generating an ultrasound image based on the derived change in the center frequency at the depth; and
- displaying the ultrasound image including an indicator for indicating the detected gas pocket.

* * * * *